(12) United States Patent
Miklos et al.

(10) Patent No.: US 11,275,977 B1
(45) Date of Patent: Mar. 15, 2022

(54) SYSTEM AND METHOD FOR ON DEMAND PRODUCTION OF CUSTOM INDICATOR ASSAYS

(71) Applicant: Combat Capabilities Development Command, Chemical Biological Center, Apg, MD (US)

(72) Inventors: Aleksandr E Miklos, Baldwin, MD (US); Gary K Kilper, Edgewood, MD (US); Charles E Davidson, Towson, MD (US); Christian J Whitchurch, Los Gatos, CA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 17/150,515

(22) Filed: Jan. 15, 2021

Related U.S. Application Data

(60) Provisional application No. 62/962,308, filed on Jan. 17, 2020.

(51) Int. Cl.
| | |
|---|---|
| *G06F 3/12* | (2006.01) |
| *G06K 15/02* | (2006.01) |
| *G06F 3/0482* | (2013.01) |
| *G06K 15/10* | (2006.01) |
| *G01N 21/78* | (2006.01) |
| *G06T 7/00* | (2017.01) |
| *G06F 16/245* | (2019.01) |

(Continued)

(52) U.S. Cl.
CPC .......... *G06K 15/021* (2013.01); *G01N 21/78* (2013.01); *G06F 3/0482* (2013.01); *G06F 16/22* (2019.01); *G06F 16/245* (2019.01); *G06K 15/102* (2013.01); *G06K 15/1803* (2013.01); *G06K 15/1823* (2013.01); *G06T 7/0012* (2013.01); *G16H 10/40* (2018.01)

(58) Field of Classification Search
CPC .............. G06K 15/021; G06K 15/102; G06K 15/1803; G06K 15/1823; G16H 10/40; G06F 16/22; G06F 16/245; G06F 3/0482; G01N 21/78; G06T 7/0012
USPC ................................................ 358/1.1–1.18
See application file for complete search history.

(56) References Cited

U.S. PATENT DOCUMENTS

| | | | |
|---|---|---|---|
| 8,098,390 B1 * | 1/2012 | Yacoub | G06Q 30/0241 358/1.15 |
| 2003/0113713 A1 * | 6/2003 | Glezer | G01N 33/54373 435/5 |

(Continued)

*Primary Examiner* — Gabriel I Garcia
(74) *Attorney, Agent, or Firm* — Ulysses John Biffoni

(57) ABSTRACT

A system and method for on-demand production of custom indicator assays including a computing device for receiving a user specified analyte for which the assay will test, a database accessible via the computing device and containing indicator response data for a variety of analytes and potential interferents, and a printer operably connected to the computing device for printing an optimized combination of indicators onto a substrate based on the indicator response data of the database for a user specified analyte and any user specified potential interferents. The method includes receiving in a user interface at least one user specified analyte; querying the database to determine an optimized combination of indicators to test for the at least one user specified analyte; and printing from a printer the optimized combination of indicators onto a substrate.

21 Claims, 4 Drawing Sheets

(51) Int. Cl.
*G16H 10/40* (2018.01)
*G06F 16/22* (2019.01)

(56) References Cited

U.S. PATENT DOCUMENTS

| | | | | |
|---|---|---|---|---|
| 2009/0278880 | A1* | 11/2009 | Dijksman | B01L 3/0268 |
| | | | | 347/14 |
| 2011/0301441 | A1* | 12/2011 | Bandic | A61B 5/4875 |
| | | | | 600/306 |
| 2015/0039325 | A1* | 2/2015 | Longman | G16H 70/40 |
| | | | | 705/2 |
| 2016/0365006 | A1* | 12/2016 | Minturn | G09B 5/00 |
| 2018/0300423 | A1* | 10/2018 | Dufour | G06Q 30/0251 |

* cited by examiner

SYSTEM AND METHOD FOR ON DEMAND PRODUCTION OF CUSTOM INDICATOR ASSAYS

RELATED APPLICATIONS

This application claims priority benefit of U.S. Provisional Application Ser. No. 62/962,308 filed Jan. 17, 2020; the contents of which are hereby incorporated by reference.

GOVERNMENT INTEREST

The invention described herein may be manufactured, used, and/or licensed by or for the United States Government.

FIELD OF THE INVENTION

The present invention generally relates to color changing indicator assays and more particularly to a system and method for on-demand printing of customized color changing indicator assays algorithmically formulated to include an optimized combination of indicators to detect one or more analytes while avoiding potential interferents.

BACKGROUND OF THE INVENTION

The detection of a wide variety of analytes is an important endeavor in the fields of medical diagnostics, air and water quality monitoring, food and beverage testing, biothreat detection, biosensing, drug screening, environmental monitoring, forensic investigation, military defense, and so forth. Diagnostic test assays have been created to detect a broad range of chemical and biological agents. The majority of these test assays attempt to detect and/or quantify the presence of particular analytes by producing a color change or visible line or zone signifying the presence or level of the analyte. In the case of multiple analytes, several potential lines or zones of color change are noted.

These test assays are used or activated in a variety of ways. Dependent upon what test and protocol the user is employing, they may dip the assay into a fluid, apply fluid using a dropper, place the assay on a fluid (e.g., blood drop on finger), or expose the assay to ambient conditions. Once the test is activated and the sample is added, a set time is generally allowed to elapse. After this set time, the user generally visually inspects the test strip for color changes in the designated regions. These color changes are compared to a reference that indicates threshold levels for quantified analyte levels.

These tests have been in use for several years and continue to be a favored method for detecting and/or quantifying the presence of particular analytes due to their ease of use. Furthermore, an increasing number of analytes may be tested for using color-changing indicator chemistry ranging from drug metabolites, pregnancy hormones, anthrax, *E. coli*, blood glucose, pool pH and chlorine, etc. However, due to the costs associated with mass production and distribution, only a few highly common tests, including litmus paper and the U.S. Army's M8 paper, are commercially available. Additionally, the physical embodiment, including shape, size, and material, of these widely available test assays is likewise limited generally to a particular common application for each analyte test assay. Given the limited number of available testing products that only target a few common chemicals, false positives are unfortunately very common. That is, it is difficult to design and produce a test assay that avoids interferents that result in such false positives. Additionally, given the limited physical embodiments of these limited test assays, the applicability and practicality of their use is also limited.

Inkjet printing is a very promising dispensing methodology being a gentle and straightforward solution-drop deposition technique, enabling fragile chemical and biological materials to be printed on solid surfaces. However, such attempts have not achieved optimized assays that avoid interferents that result in false-positives and have still only been capable of producing limited physical embodiments, including shape, size, and material.

Thus, there exists a need for on-demand production of custom color-changing indicator assays that are able to target a wide variety of analytes, avoid specified potential interferents thereby reducing instances of false-positive tests, and are available in a customizable physical embodiment including shape, size, and material.

SUMMARY OF THE INVENTION

A system for on-demand production of custom indicator assays is provided that includes a computing device, a database accessible via the computing device, a printer operably connected to the computing device, and a selection of indicator cartridges for that printer, available to the operator of the device. The database contains indicator response data for a variety of analytes and potential interferents, and the printer is configured to print an optimized combination of indicators onto a substrate based on the indicator response data of the database for a user specified analyte and any user specified potential interferents.

According to embodiments, the database is built by exposing numerous indicators to a chemical library guided by an algorithm; imaging the exposed numerous indicators to produce raw image data; analyzing the raw image data to develop indicator response data of each indicator of the numerous indicators in response to each chemical of the chemical library; and inputting the indicator response data into the database.

The present disclosure also provides a method for on-demand production of custom indicator assays. The method includes receiving in a user at least one user specified analyte for which a custom indicator assay will test; querying a database containing indicator response data for a variety of analytes and potential interferents to determine an optimized combination of indicators to test for the at least one user specified analyte; and printing from a printer the optimized combination of indicators onto a substrate. According to embodiments, the method also includes first building the database as described. According to further embodiments, the method additionally includes, prior to printing, instructing the user to install indicator containing cartridges into the printer, the indicator containing cartridges containing the indicators needed to create the optimized combination of indicators.

BRIEF DESCRIPTION OF THE DRAWINGS

The present invention is further detailed with respect to the following drawings that are intended to show certain aspects of the present invention but should not be construed as a limit on the practice of the present invention.

DESCRIPTION OF THE INVENTION

Figure 1:
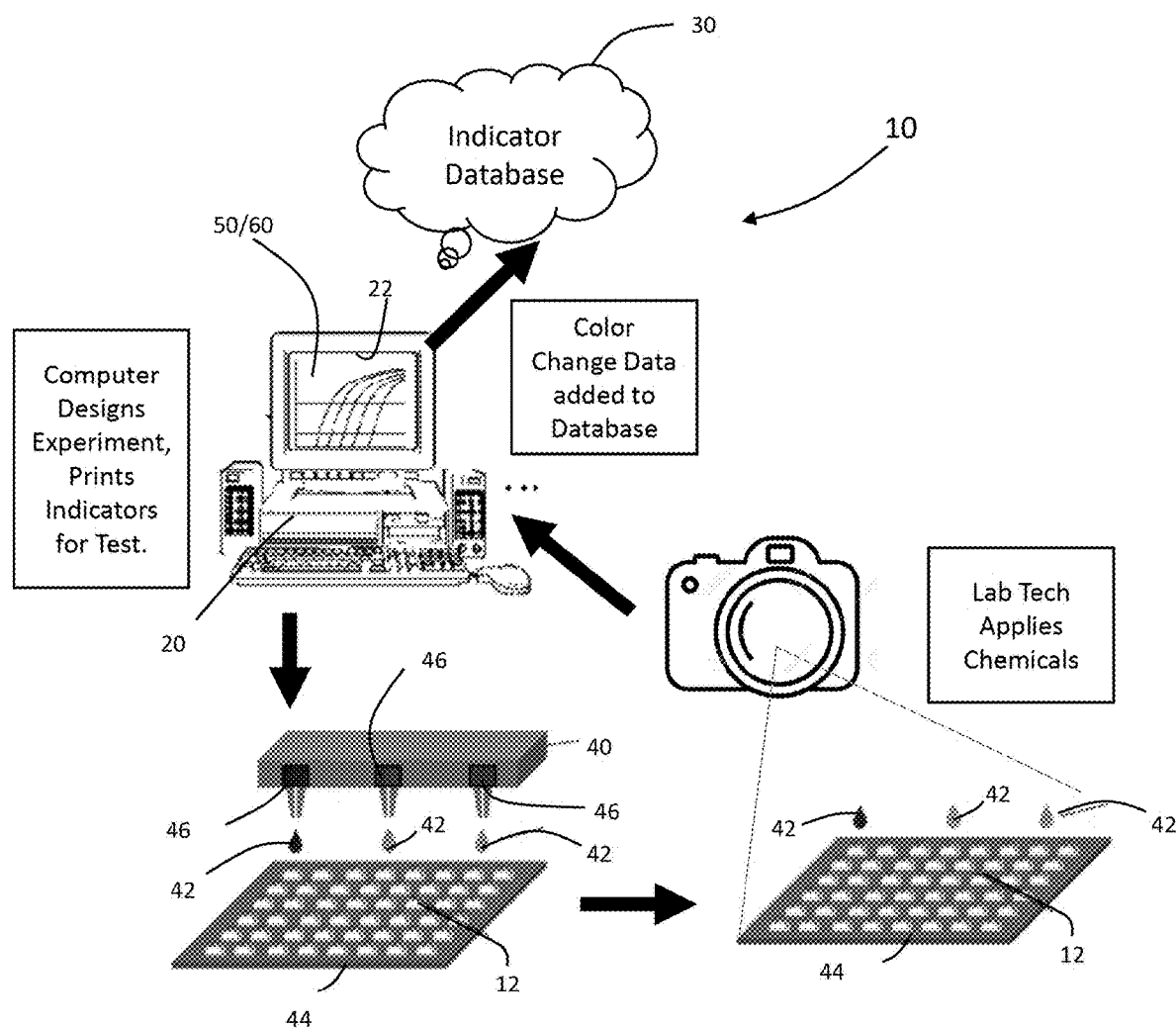
FIG. 1 is a schematic representation of a system for on-demand production of custom indicator assays according to embodiments of the present disclosure.

The present invention has utility as a system and method for on-demand production of custom color-changing indicator assays that are able to target a wide variety of analytes, avoid specified potential interferents, and are available in a customizable physical embodiment including shape, size, and material, while also reducing the likelihood of a false-positive test for the user specified analyte as a result of potential interferents. The present invention also has utility as high-speed, miniaturized, low-cost, and high-throughput solution for producing custom indicator assays and has important applicability in fields such as biosensing, drug screening, environmental monitoring, forensic investigation, and military defense.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As shown in FIG. 1, a system 10 for on-demand production of custom indicator assays 12 according to embodiments of the present disclosure includes a computing device 20, a database 30 accessible via the computing device 20, and a printer 40 operably connected to the computing device 20. According to embodiments, the database 30 is a web-based database, is stored on a cloud network, or is stored in the local memory of the computing device 20. According to still other embodiments, the database 30 is accessible via the computing device 20 through an internet web browser, a software application stored on the computing device, or a software program that is saved to the computing device 20. According to other embodiments, the remote computing device 20 is configured to establish connection to the database 30 from access points in a network, such as cellular base stations, Wi-Fi access points, and the like, using at least one of the radio access technologies or an internet connection, such as a 2G, 3G, or LTE connection. According to embodiments the operable connection between the computing device 20 and the printer 40 is a wired connection. Alternatively, the operable connection is established wirelessly, such by a conventional radio access technology, such as Long Term Evolution (LTE), wireless local area network (WLAN) technology, such as 802.11 Wi-Fi and the like, Bluetooth, Bluetooth low energy (BT-LE), near field communications (NFC), and any other radio access technologies or an internet connection, such as a 2G, 3G, or LTE connection.

According to some inventive embodiments, the computing device 20 is any of a computer, a smart phone, or a tablet. The computing device may be implemented as a mobile, wireless device such as a smart phone, a laptop, or a tablet, or may be implemented as a stationary device, such as a personal computer and the like. According to embodiments as shown in FIG. 1, the computing device 20 includes a screen 22 that is configured to display a user interface 50, 60. A user interface operative in the present invention illustratively includes a graphical user interface, touchscreen graphical user interface, menu-drive interface, command line interface, conversational user interface, or a combination of any of the aforementioned.

Figure 3A:
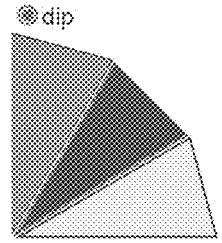
FIGS. 3A and 3B are photographs showing a graphical user interface (GUI) used with a system and method for on-demand production of custom indicator assays according to embodiments of the present disclosure.
Figure 3B:
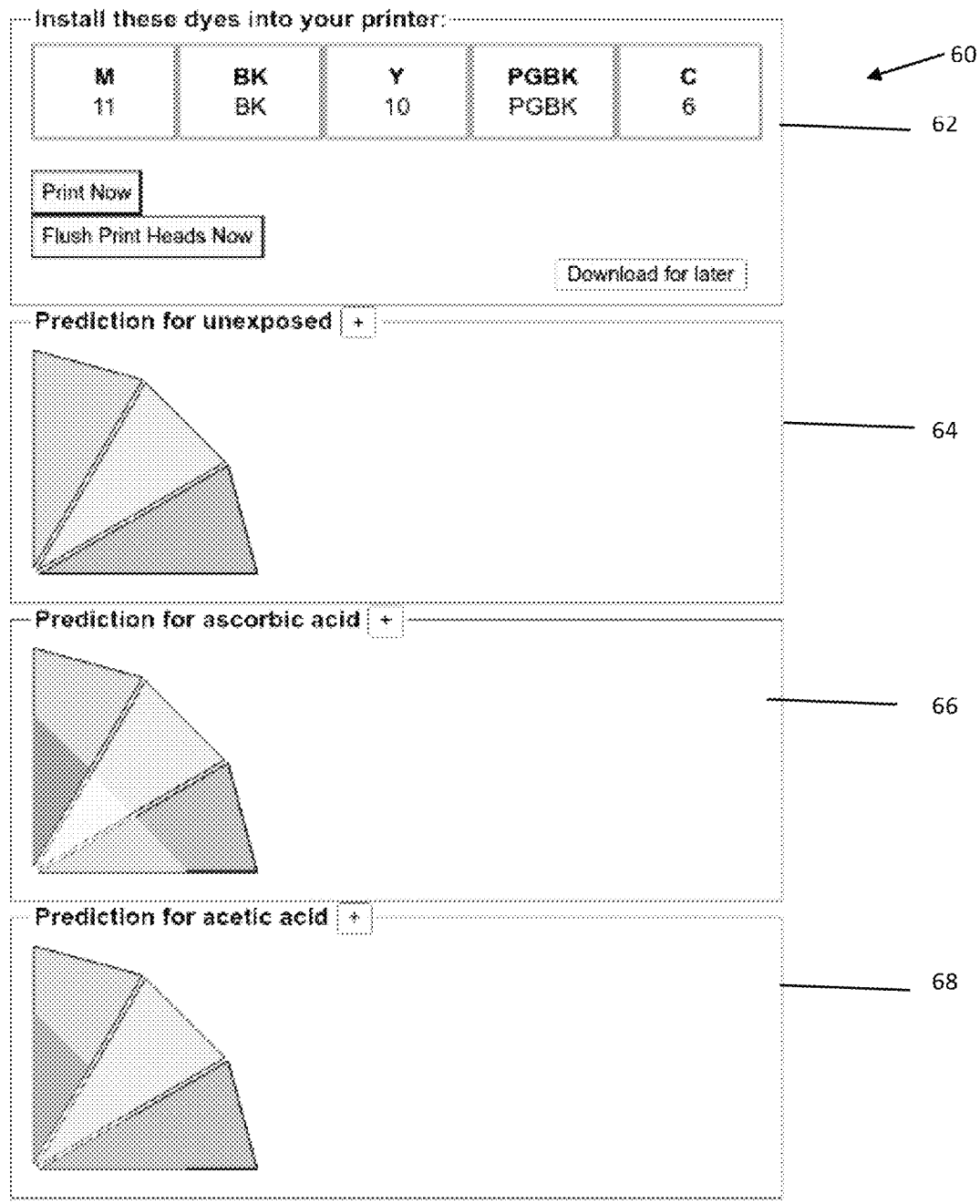

The details of the user interface are shown in FIGS. 3A and 3B. Within an input user interface 50, a user is able to specify numerous parameters of customization for each desired custom assay. For example, within the input user interface 50 a user is able to select a specified analyte for which the custom indicator assay will test. As shown in block 51 of the input user interface 50 in FIG. 3A, a user may select from a variety of analyte options illustratively including bleach, citric acid, isopropanol, sodium hydroxide, malic acid, a commercial cleaning product, trimethyl phosphate, deionized water, acetic acid, aqueous film forming foams (AFFF), ascorbic acid, a commercial firearm lubricant and cleaner, tap water, thiodiglycol, HCl, lactic acid, glyphosate solution, 2-butoxyethanol solution, sugar water drink flavors, tartaric acid, glass cleaner formulations, pine oil based cleaner, β-mercaptoethanol, and chalk. It will be understood that the list of selectable analytes may include any other chemical or biological material for which color-changing indicator chemistry is known, such as those described in F. Feigl "Spot Tests in Organic Analysis," ISBN 978-0-444-40209-7, which is hereby incorporated by reference. Similarly, a user is able to specify any potential interferent chemicals or biological agents that may otherwise result in a false positive for the analyte on the test assay. For example, as shown in box 52 of the input 50 shown in FIG. 3A, a user may select from a pre-selected list such as the aforementioned analytes, or others that might define a panel of interest. It will be understood that the list of selectable analytes may include any other chemical or biological material for which color-changing indicator chemistry is known. The user may select any number of potential interferents that potentially may be present in an environment in which the customer indicator assay will be used.

According to certain inventive embodiments, a user is also able to specify the state of matter of the analyte sample, for example whether the sample is a liquid matter or a vapor matter, as shown in box 53 of the input user interface 50 of FIG. 3A. Additionally, within optional box 54 of the input user interface 50 a user can specify what the analyte sample will be diluted in, for example in water, in methanol (MeOH), in isopropanol, or whether the sample will be undiluted. Furthermore, a user is able to specify a desired test type for the custom assay, that is, as shown in box 55 of FIG. 3A, a user can select whether the custom assay should be a dip type indicator assay, a spot type indicator assay, or a probe type indicator assay. Further options assay customization that can be selected by a user in the input user interface 50 include, but are not limited to, specifying a shape, size, or form-factor of the custom indicator assay. Additionally, according to certain inventive embodiments, the input user interface 50 allows a user to specify a material of the substrate 44 upon which the custom assay will be printed. For example, a user is able to specify that the substrate 44 be blotter paper, an adhesive backed material, a fabric, or any other material suitable as an assay substrate. According to certain inventive embodiments, a user is also able to select within the input user interface 50 numerous indicator cartridges 46 that are available to the user, as shown in FIG. 1. Such indicator cartridges 46 are configured to be installed into the printer 40 and are configured to dispense the contained indicator 42 from the cartridge 46 onto the substrate 44. As shown in box 56 of the input user interface 50 of FIG. 3A, the indicator cartridges are labeled by numbers, which correspond to the physical cartridges 46 configured to be installed in the printer 40. Alternatively, the cartridges may be color coded, labeled by the name of the indicator contained therein, or indexed in any other manner to permit correct installation as instructed by the software.

After the customization information has been entered by a user into the input user interface 50, an algorithm analyzes the input information and queries the database 30. The database 30 contains indicator response data for a variety of target analytes and potential interferents and is configured to algorithmically determine an optimized combination of indicators 42 to produce the desired custom assay to test for the user specified analyte while avoiding any potential interferents identified by the user. As shown in FIG. 3B, the algorithm generates an output user interface 60 that is displayed to the user on the screen 22 of the computing device 20. According to embodiments, the output user interface 60 provides instructions to the user to install a subset of the available indicator cartridges 46 into the printer 40, as shown by box 62. The subset of indicator cartridges 46 contain the indicators 42 needed to create the optimized combination of indicators to produce the custom indicator assay as determined by the algorithm and database 30. According to embodiments, the output user interface 60 also provides a prediction for what the unexposed custom indicator assay 12 will look like, as shown in box 64. According to embodiments, the output user interface 60 also provides a prediction for what the custom indicator assay 12 will look like after exposure to the specified analyte, as shown in box 66. According to embodiments, the output user interface 60 also provides a prediction for what the custom indicator assay 12 will look like when exposed to the specified interferent, as shown in box 68. By providing such predictions, the database 30 is able to remove a great deal of the subjectivity of post-test indicator assay analysis.

The algorithm process can be described as follows. When presented with a target analyte chemical ("analyte") to detect and an interferent chemical one needs to distinguish and avoid false alarms from ("interferent"), the algorithm begins searching the database for indicators. The algorithm first looks for indicators that undergo a color change in response to the analyte, and begins to rank-order these color changes using a model for human color perception, such that the rankings correspond to how different the before and after colors for each indicator would look to a human observer. The same operation is performed for the interferent chemical. The algorithm then ranks these indicators again, this time considering the difference in response between the analyte and the interferent. The final step is to select the optimal indicators, typically two or more in order to provide robust discrimination. This selection is done by co-optimizing the raw color change magnitude (the first ranking) and the difference in color change between the analyte and interferent chemicals (the second ranking). Of course, the algorithm requires the color-change database and the user input to function, and there is an adjustable threshold value for the required color change magnitude which can be manipulated. The algorithm will always return the indicators with the most apparent color change and best available color change difference between the analyte and the interferent, but this value can be set to return a "no match" message to the user when the color changes found fall beneath the minimum change necessary to be observed by eye.

For example, this algorithm has been demonstrated to generate a custom indicator assay capable of discriminating between two acids commonly used as food ingredients, i.e., ascorbic acid (Vitamin C) and malic acid (used as a coating for Sour Patch Kids). The user specified that one indicator should change for both compounds (so that they could ensure the paper substrate had been exposed) but that two of them should respond only to ascorbic acid. From a set of 18 indicators, the algorithm returned methyl Red, thionine, and a composition that contained both methylene green and neutral red. The first indicator (methyl red) started off as a golden yellow color but became bright red when exposed to either ascorbic or malic acid. Thionine starts off as a light blue color and remains so upon exposure to malic acid, but quickly loses all color upon exposure to ascorbic acid thereby producing a blue to white color transition. The methylene green and neutral red composition starts off a medium blue color, does not change for malic acid, and turns a reddish-purple color upon exposure to ascorbic acid. The assay tickets were marked with the instruction "ALL THREE MUST CHANGE" indicating that ascorbic acid is only identified if all three printed regions of the ticket changed color because of the specific indicators chosen. Thus, ascorbic acid can be differentiated from malic acid in a sample using this particular custom assay.

The printer 40, which is operatively connected to the computing device 20, is configured to print the optimized combination of indicators 42, as determined by the algorithm and database 30 based on the indicator response data of the database 30 for a user specified analyte and any user specified potential interferents, onto a substrate 44. According to embodiments, the printer 40 is an inkjet printer. Inkjet printing is a dispensing methodology that is a gentle and straightforward solution-drop deposition technique, enabling fragile chemical and biological materials to be printed on substrates 44 of a multitude of materials, as described above. It is appreciated that a printer may be able to hold numerous cartridges that vary in indicators, in some inventive embodiments, there is no need for intermediate human intervention to load indicators.

Figure 2:
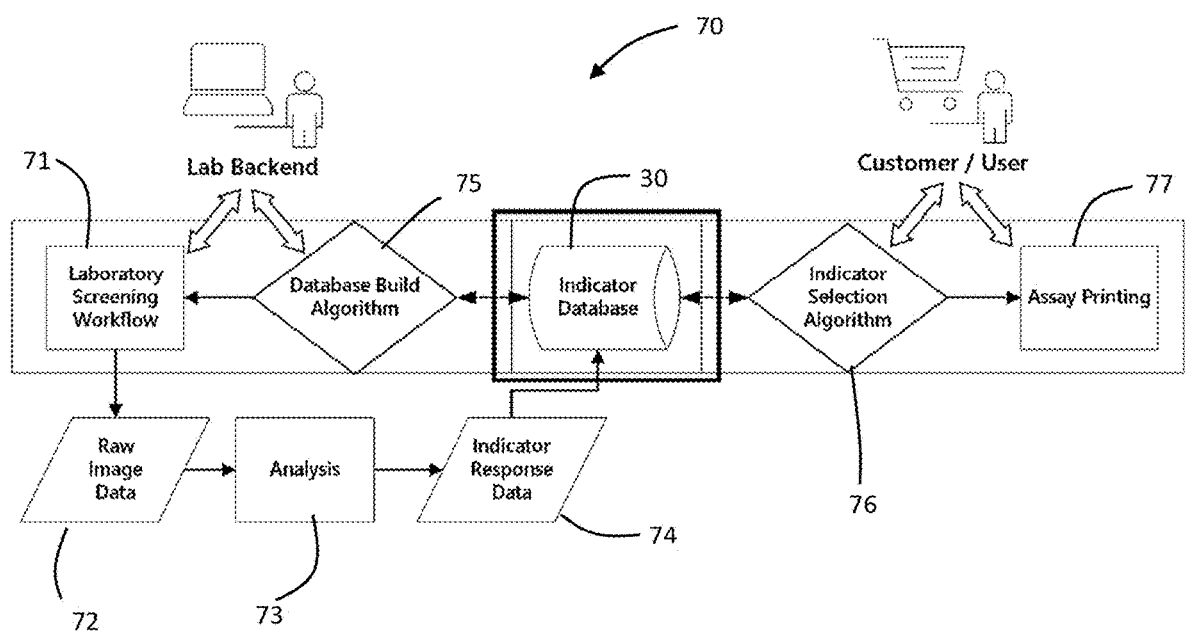
FIG. 2 is a flow chart showing a method for the population of an indicator database and also the on-demand production of custom indicator assays according to embodiments of the present disclosure.

The present disclosure also provides a method 70 for on-demand production of custom indicator assays using the system described herein. According to embodiments, the method 70 begins by building the database 30 containing indicator response data for a variety of analytes and potential interferents is built, as shown in FIG. 2. The database 30 is built by exposing a variety of indicators to a chemical library guided by an algorithm as shown at step 71. Next, the exposed indicators are imaged at step 72 by imaging software to produce raw image data of each indicator reaction. Next, the raw image date is analyzed at step 73 to develop indicator response data of each indicator of the numerous indicators in response to each chemical of the chemical library. That indicator response data is then inputted into the database 30 at step 74. This process may be repeated, as shown in step 75, as many times as is needed to record all combination of indicator reactions to all chemicals in the chemical library.

Once the database 30 has been built on the backend, the method for on-demand production of custom indicator assays continues on the front end when a user interacts with the input user interface 50 on the computing device 20. That is, the method 70 includes receiving in a user interface 50 at least one user specified analyte for which a custom indicator assay 12 will test. The method proceeds by querying the database 30 using an indicator selection algorithm at step 76 to determine an optimized combination of indicators to test for the at least one user specified analyte. According to embodiments, the method includes instructing the user to install indicator containing cartridges 46 into the printer 40, for example on an output user interface 60 as shown in FIG. 3B. Finally, the method includes printing from the printer 40 the optimized combination of indicators 42 onto the substrate 44 at step 77.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention but is not meant to be a limitation upon the practice thereof. The following claims, including all equivalents thereof, are intended to define the scope of the invention.

The invention claimed is:

1. A system for on-demand production of custom indicator assays, the system comprising:
   a computing device;
   a database accessible via the computing device, the database containing indicator response data for a plurality of analytes and potential interferents; and
   a printer operably connected to the computing device, the printer configured to print an optimized combination of indicators onto a substrate based on the indicator response data of the database for a user specified analyte and any user specified potential interferents.

2. The system of claim 1, wherein the computing device is any one of a computer, a smart phone, or a tablet.

3. The system of claim 1, wherein the computing device is configured to display a user interface.

4. The system of claim 3, wherein the user interface allows a user to select any combination of a size, a shape, and a material of the substrate of the custom indicator assay.

5. The system of claim 3, wherein the user interface is a graphical user interface.

6. The system of claim 5, wherein the graphical user interface allows a user to select the specified analyte for which the custom indicator assay will test and any potential interferents present in an environment in which the custom indicator assay will be used.

7. The system of claim 5, wherein the graphical user interface allows a user to select a form-factor of the custom indicator assay.

8. The system of claim 1, further comprising a plurality of indicator-containing cartridges configured to be installed in the printer.

9. The system of claim 1, wherein the printer is an inkjet printer.

10. The system of claim 1, wherein the custom indicator assay is a color-changing indicator assay.

11. A method for on-demand production of custom indicator assays, the method comprising:
    receiving in a user interface at least one user specified analyte for which a custom indicator assay will test;
    querying a database containing indicator response data for a plurality of analytes and potential interferents to determine an optimized combination of indicators to test for the at least one user specified analyte; and
    printing from a printer the optimized combination of indicators onto a substrate.

12. The method of claim 11, further comprising, prior to printing, instructing the user to install a plurality of indicator-containing cartridges into the printer, the plurality of indicator-containing cartridges containing the indicators needed to create the optimized combination of indicators.

13. The method of claim 11, wherein the user interface is presented to a user on a computing device.

14. The method of claim 13, wherein the computing device is any one of computer, smart phone, or a tablet.

15. The method of claim 11, further comprising receiving in the user interface at least one user specified potential interferent that may be present in an environment in which the custom indicator assay will be used.

16. The method of claim 11, further comprising receiving in the user interface a user specified size of the custom indicator assay.

17. The method of claim 11, further comprising receiving in the user interface a user specified shape of the custom indicator assay.

18. The method of claim 11, further comprising receiving in the user interface a user specified substrate material of the custom indicator assay.

19. The method of claim 11, further comprising receiving in the user interface a user specified form-factor of the custom indicator assay.

20. The method of claim 11, wherein the optimized combination of indicators reduces the likelihood of a false-positive test for the user specified analyte as a result of potential interferents.

21. The method of claim 11, further comprising first building the database containing indicator response data for a plurality of analytes and potential interferents, wherein building the database comprises:
    exposing a plurality of indicators to a chemical library guided by an algorithm;

imaging the exposed plurality of indicators to produce raw image data;

analyzing the raw image data to develop indicator response data of each indicator of the plurality of indicators in response to each chemical of the chemical library; and inputting the indicator response data into the database.

\* \* \* \* \*